United States Patent
Doyle et al.

(10) Patent No.: US 12,133,938 B2
(45) Date of Patent: Nov. 5, 2024

(54) ULTRAVIOLET CYCLONIC FLUID DOSING SYSTEM

(71) Applicant: Violett Inc., Gig Harbor, WA (US)

(72) Inventors: Branden Lee Doyle, Gig Harbor, WA (US); Christopher Sean Doyle, Bremerton, WA (US)

(73) Assignee: Violett Inc., Gig Harbor, WA (US)

( * ) Notice: Subject to any disclaimer, the term of this patent is extended or adjusted under 35 U.S.C. 154(b) by 353 days.

(21) Appl. No.: 17/574,159

(22) Filed: Jan. 12, 2022

(65) Prior Publication Data

US 2022/0218865 A1    Jul. 14, 2022

Related U.S. Application Data

(60) Provisional application No. 63/136,637, filed on Jan. 12, 2021.

(51) Int. Cl.
| | | |
|---|---|---|
| *A61L 9/20* | (2006.01) | |
| *A61L 9/18* | (2006.01) | |
| *G10K 11/162* | (2006.01) | |

(52) U.S. Cl.
CPC ...... *A61L 9/20* (2013.01); *A61L 9/18* (2013.01); *G10K 11/162* (2013.01); *A61L 2209/12* (2013.01); *A61L 2209/14* (2013.01)

(58) Field of Classification Search
CPC ..... A61L 2/10; A61L 2/20; A61L 2/24; A61L 2/26; A61L 2/0047; A61L 2/081;
(Continued)

(56) References Cited

U.S. PATENT DOCUMENTS

| 8,808,432 B2 | 8/2014 | Rotter et al. |
|---|---|---|
| 10,368,557 B2 | 8/2019 | Foret |

(Continued)

FOREIGN PATENT DOCUMENTS

| CN | 111617590 | 9/2020 | |
|---|---|---|---|
| CN | 111617590 A | * 9/2020 | ........... B01D 50/004 |

(Continued)

OTHER PUBLICATIONS

International Search Report and Written Opinion of the International Searching Authority dated Apr. 28, 2022, in International Patent Application No. PCT/US22/12147, 9 pages.

*Primary Examiner* — David E Smith
*Assistant Examiner* — Hsien C Tsai
(74) *Attorney, Agent, or Firm* — Benedict R. Dugan; Lowe Graham Jones PLLC

(57) ABSTRACT

An ultraviolet cyclonic fluid dosing system for disinfecting fluid materials is described. The dosing system includes a dosing chamber that includes a cylindrical chamber portion and a conical chamber portion. The cylindrical chamber portion has a fluid outlet and a fluid inlet that causes fluid material to enter the upper chamber and travel a helical path down through the upper chamber and into the conical chamber, from where it travels upward in exits through the fluid outlet. As the fluid material passes through the cylindrical and conical chambers, it is dosed with disinfecting ultraviolet light. The system advantageously increases the exposure time of the fluid material to the disinfecting ultraviolet light is increased as compared to non-cyclonic dosing systems having the same volume.

19 Claims, 11 Drawing Sheets

(58) Field of Classification Search
CPC . A61L 2/0094; A61L 9/18; A61L 9/20; A61L 9/205; A61L 2209/11; A61L 2209/12; A61L 2209/14; A61L 2209/111; A61L 2209/211
See application file for complete search history.

(56) References Cited

U.S. PATENT DOCUMENTS

| | | |
|---|---|---|
| 2018/0055956 A1 | 3/2018 | Cooper et al. |
| 2018/0160694 A9 * | 6/2018 | Foret ................ C02F 1/30 |
| 2021/0188050 A1 * | 6/2021 | Mou ............ B01D 39/2055 |

FOREIGN PATENT DOCUMENTS

| | | | |
|---|---|---|---|
| KR | 10-2016-0026347 | 3/2016 | |
| WO | 2017/051774 | 3/2017 | |
| WO | WO-2017051774 A1 * | 3/2017 | ........... A61L 2/10 |

* cited by examiner

ULTRAVIOLET CYCLONIC FLUID DOSING SYSTEM

CROSS-REFERENCE TO RELATED APPLICATION

This application claims priority from U.S. Provisional Patent Application No. 63/136,637 filed Jan. 12, 2021, the entire content of which is incorporated herein by reference.

FIELD OF THE INVENTION

This invention relates to the field of fluid (liquid, gas, fluidized solids) disinfection, filtration and processing. Specifically, this invention relates to utilization of ultraviolet light in the treatment of fluids. Treatment includes filtration of debris and particles, disinfection of pathogens (viruses, bacteria, mold, fungus, etc.) within the fluid, and dosing fluids or solids in the fluids with ultraviolet light. Dosing fluids and entrained solids for purposes outside of disinfection includes curing or chemically processing/altering the fluid with ultraviolet light. A specific use is in the field of disinfection of pathogens in water and air.

BACKGROUND

Filtration, disinfection, and ultraviolet dosing of fluids is common within the art of fluid processing. Typical systems can be standalone, or implemented in a larger system to accomplish disinfection, filtration or ultraviolet dosing of fluids.

Filtration of fluids is accomplished with mechanical filtration (filter media beds, HEPA or similar fiber/fabric filter assemblies, osmotic/membrane filters, mechanical separators), electrostatic filtration, and chemical filtration. Typical implementations of filtration methods use piping or ducting connected to the filtration chamber/assembly/volume in which the fluid (gas or liquid) is pulled through using pumps or fans. Mechanical fluid filtration typically uses permeable filter media, membranes, or fabric to remove debris or particulate from a fluid. Electrostatic filters charge debris and particles as they enter the filtration assembly and are electrostatically collected on collection plates of opposing charge. Chemical filtration uses chemical flocculates to form larger or denser conglomerates of debris and particles which are then collected by mechanical separation or settle into a settling volume and are removed.

Cyclonic separators are a type of mechanical particle separator and are commonly used to remove dust and entrained particles from industrial fluid streams. Cyclonic separators typically comprise a tangential inlet to a cylindrical transition area, a cylindrical volume, a lower conical volume and a central outlet. When fluid traverses through the cyclonic separator, a helical flow path is generated. The entrained dust and particles lose energy to friction from collisions with the cyclonic separator's inner wall while transitioning from tangential to radial velocity components, and also during boundary layer interactions. The decelerating particles and dust separate from the fluid flow, and exit through the base into a particle collection chamber. The fluid transitions vertically into the central outlet which is connected to a downstream fan or pump.

Disinfection of fluids in prior art has been accomplished by chemical, thermal, and germicidal ultraviolet light processes, as well as through mechanical, and electrostatic filtration processes. Disinfection of fluids are most commonly performed on water and air. Mechanical filter disinfection is performed by physically removing pathogens, such as viruses, bacteria, fungus or mold, from the fluid stream by entrapping the pathogen into filter material. Electrostatic filter disinfection is primarily used for gases like air, and functions in a similar way to the mechanical filtration methods described above, by entrapping the pathogen. Chemical, thermal and germicidal ultraviolet disinfection methods are implemented for disinfection in both liquids and gases (mainly water and air). Chemical disinfection methods add chemicals that have disinfectant properties to the liquid, which is most commonly water. Thermal disinfection is performed by pumping the fluid into a heated volume to allow the fluid temperature to increase, resulting in inactivation (disinfection) of pathogens.

Germicidal ultraviolet disinfection is common for liquids like water, and less common for gases like air. Ultraviolet disinfection of liquids, most commonly water, is accomplished by emitting germicidal ultraviolet light into a holding tank or vessel, which will disinfect pathogens in the fluid if a proper dose is received. In-line germicidal ultraviolet systems are also used to disinfect liquid by pumping it through an in-line assembly, which has a germicidal ultraviolet light emitter and typically an ultraviolet reflective lining. As the liquid passes through the in-line disinfection assembly, the pathogens are inactivated by a certain percentage based on dose received. Thus, in-line systems are typically implemented in circulating systems. Germicidal ultraviolet air disinfection systems are most typically connected in-line into a ventilation system, or integrated into a piece of ventilation equipment like a standalone air handling system or air conditioning unit. Ultraviolet disinfection systems typically comprise an ultraviolet light emitter, and are sometimes lined with reflective housing to and from a disinfection volume. The reflective material is typically polished aluminum, or, less commonly, advanced ultraviolet reflective materials such as sintered PTFE (polytetrafluoroethylene) or Barium Sulfate ($BaSO_4$) based coating. Undisinfected air is pulled or pumped through the disinfection volume and the air receives a small dose of ultraviolet light. A currently effective use of germicidal ultraviolet disinfection is the disinfection of fixed surfaces within ventilation systems that can grow or harbor pathogens like fungus, mold, or, at times, bacteria or viruses. An ultraviolet light emitter is directed toward the surface requiring disinfection. The emitter provides a sufficient dose of ultraviolet light to inactivate or prevent growth of pathogens on the subject surface within the ventilation system.

Disadvantages in the prior art are largely in the field of fluid disinfection. A disadvantage of mechanical and electrostatic disinfection systems is the process effectiveness being dependent on the size of the pathogen. The systems require specific configuration, filter material and operational parameters to entrap specific pathogens in the system. The systems require regular maintenance (cleaning and replacement of filter material) as well as monitoring to ensure system effectiveness.

A disadvantage of mechanical filtration is that it requires extensive HEPA ("High-Efficiency Particulate Air") or ULPA ("Ultra Low Particulate Air") filter assemblies in combination with a complex ventilation system to meaningfully remove pathogens from air. For liquids, the system typically requires extensive filtration banks and/or reverse osmosis filtration systems in addition to powerful pumps.

Disadvantages of chemical fluid disinfection are the hazards posed by the chemicals, and the requirement of a skilled and/or trained operator in the process to ensure the fluid is not hazardous following the chemical disinfection treatment.

Disadvantages of thermal disinfection include the energy intensiveness, and the requirement for cooling of the fluid post-disinfection. Both come with significant added cost. Thermal disinfection is also not usable for thermally sensitive fluids, such as biological fluids including but not limited to blood or blood products.

A disadvantage of the current state of germicidal ultraviolet disinfection systems is the tank or vessel disinfection system requiring processing of the liquid in batches, and typically having low volumetric disinfection rates. While in-line germicidal ultraviolet disinfection systems have increased volumetric flow rates, their significant disadvantage is their limited ability to provide a sufficient dose based on the short period of time pathogens are exposed to the ultraviolet light.

Typically, air ventilation systems require the disinfection process to be in-line with the ventilation system, or else the disinfection system is configured into a standalone air handling system. The disadvantage of current methods of germicidal ultraviolet disinfection in air applications is that both in-line and standalone air disinfection systems provide an insufficient dose of ultraviolet light to effectively inactivate pathogens. The reason for the insufficient dose is due to extremely short residence time when the air is inside of the disinfection volume. To reach a sufficient dose of ultraviolet light, the length of the disinfection volume must be prohibitively long. Along with additional system length required to achieve an appropriate dose, an extensive network of ultraviolet emitters would be required to illuminate the length of the system. While the described system is technically feasible, the system's prohibitively large size and cost, for both ventilation systems or standalone air handling systems, would be highly impractical.

The subject invention seeks to provide an improved fluid disinfection system that addresses the disadvantages of the prior art.

BRIEF SUMMARY

A first embodiment provides an ultraviolet cyclonic fluid dosing system, comprising a dosing chamber that includes: an upper cylindrical cyclonic chamber having a tangential fluid inlet and a central fluid outlet; a lower conical cyclonic chamber coupled to the upper chamber; and at least one ultraviolet-light emitter positioned within the dosing chamber, the emitter configured to dose a fluid material (e.g., air, water) with ultraviolet light, wherein the fluid material enters the fluid inlet and travels through a helical path through the dosing chamber. In some embodiments, the upper and lower chambers are coated on an inner surface with a reflective material, which may include one or more of sintered PTFE polymer and Barium Sulfate. The chamber may be configured to cause the fluid material to travel in a helical path downwards through the upper chamber and then downwards into the lower chamber, where the fluid material transitions to travel upwards and exit the central fluid outlet. The system may include one or more additional dosing chambers, each including at least one ultraviolet light emitter. The dosing chambers may be connected in parallel, such that a quantity of fluid input to the system is divided amongst the dosing chambers. The dosing chambers may be connected in series, such that a quantity of fluid input into the system passes through each of the dosing chambers in sequence.

A second embodiment provides an electromagnetic cyclonic fluid dosing system, comprising (1) a dosing chamber that includes: an upper cylindrical cyclonic chamber having a first end, a second end, a tangential fluid inlet, and a cylindrical central fluid outlet, wherein the central fluid outlet is positioned at the first end of the cylindrical chamber; and a lower conical cyclonic chamber having a first end and a narrower second end, wherein the first end of the lower chamber is coupled to the second end of the upper chamber; and (2) at least one electromagnetic radiation emitter positioned within the dosing chamber, the emitter configured to dose a fluid material with electromagnetic radiation, wherein the chamber is configured to cause the fluid material to travel in a helical path downwards from the first end through the upper chamber and then downwards through the second end and into the lower chamber, where the fluid material transitions to travel upwards and exit the central fluid outlet. The electromagnetic radiation may be one or more of ultraviolet light or gamma radiation. The upper chamber may have a diameter that is 130-150 mm. The upper and lower chambers together may have a length of 290-310 mm. The cylindrical central fluid outlet may have a length of 90-100 mm and a diameter of 38-42 mm.

A third embodiment provides a cyclonic system for disinfecting air, the system comprising: (1) a dosing chamber having an upper portion and a lower portion coupled to the upper portion, the upper portion having a cylindrical inner surface, the lower portion having a conical inner surface, the upper portion defining an air inlet and an air outlet, the dosing chamber defining a central axis that extends through an upper interior space defined by the center of the upper portion and a lower interior space defined by the center of the lower portion and that intersects the air outlet, the air inlet disposed closer to the cylindrical inner surface than the central axis and configured to introduce air into the upper portion such that the air travels about the central axis along the cylindrical inner surface of the upper portion at a downward angle to the lower portion and, after the air reaches the lower portion, travels along the central axis through the upper portion to the air outlet to exit the dosing chamber, whereby a duration that the air spends in the lower portion and about the air outlet is increased; (2) an array of ultraviolet-light emitters disposed in the upper portion along a perimeter of the fluid outlet; and (3) an ultraviolet-light emitter disposed in the lower portion along the central axis, whereby an exposure time of the air to ultraviolet light is increased. The upper portion may include a cylindrical portion that extends downward from a top of the upper portion along the central axis to define the air outlet lower than the air inlet, whereby cyclonic flow of the air is increased and an exposure time of the air to ultraviolet light is increased. The lower portion may include an extension that protrudes along the central axis from a bottom of the lower portion and that supports the ultraviolet-light emitter disposed in the lower portion, whereby cyclonic flow of the air is increased and an exposure time of the air to ultraviolet light is increased. The cylindrical inner surface and the conical inner surface may be defined by a reflective material, whereby an amplitude of ultraviolet light in the upper chamber and the lower chamber is increased. The system may further include a housing that surrounds the dosing chamber, the housing defining a bottom opening and inner space disposed between the housing and the dosing chamber, the bottom opening containing a filter configured to mechanically filter air entering the housing, the inner space fluidly coupling the filter and the air inlet. The system may further include a sound damping material that lines a surface of the housing.

BRIEF DESCRIPTION OF THE DRAWINGS

The embodiments of this invention are described below and reference the attached drawings.

DETAILED DESCRIPTION

Figure 1:
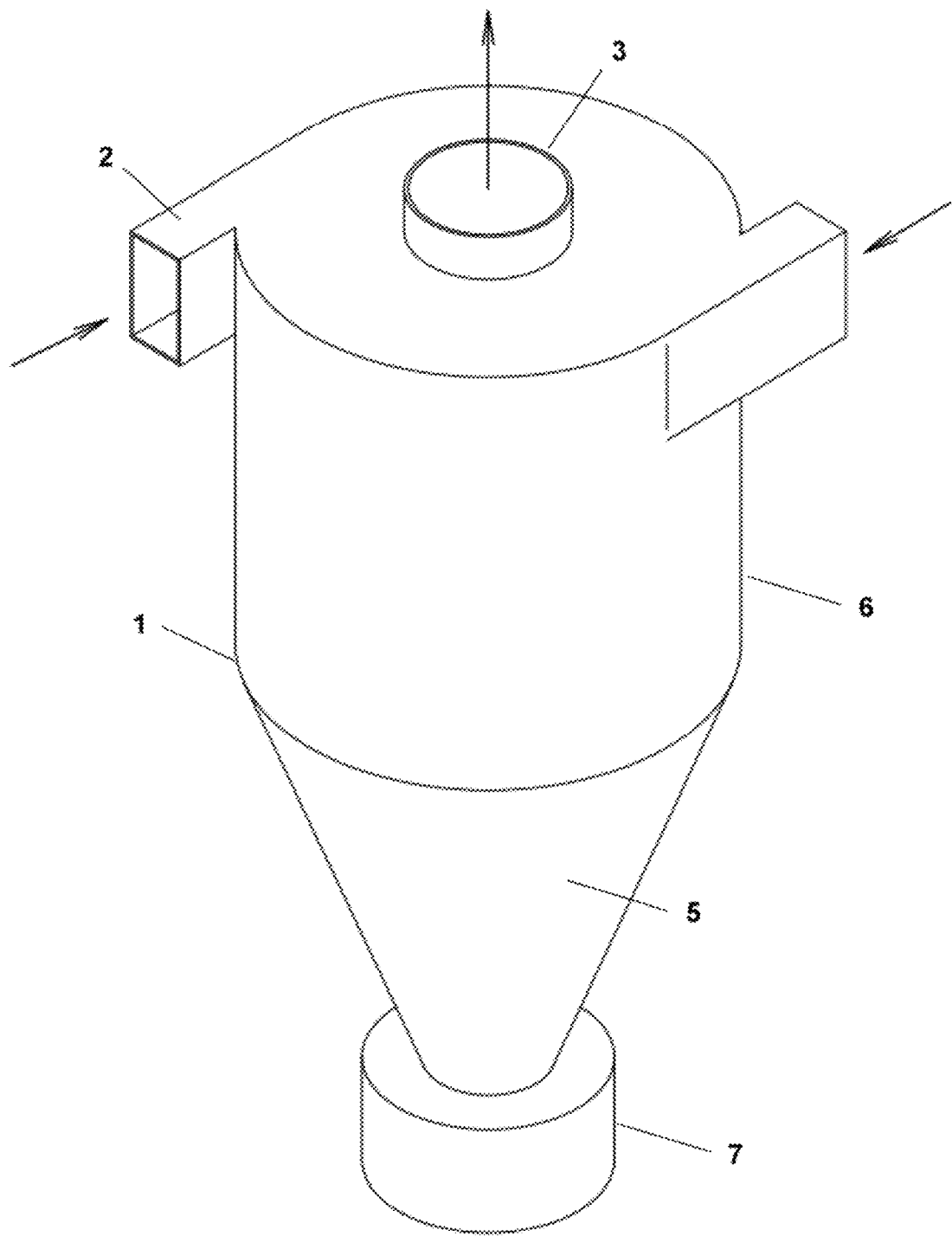
FIG. 1 shows the principal components of the ultraviolet cyclonic fluid dosing system's cyclonic dosing chamber according to one embodiment.
Figure 2:
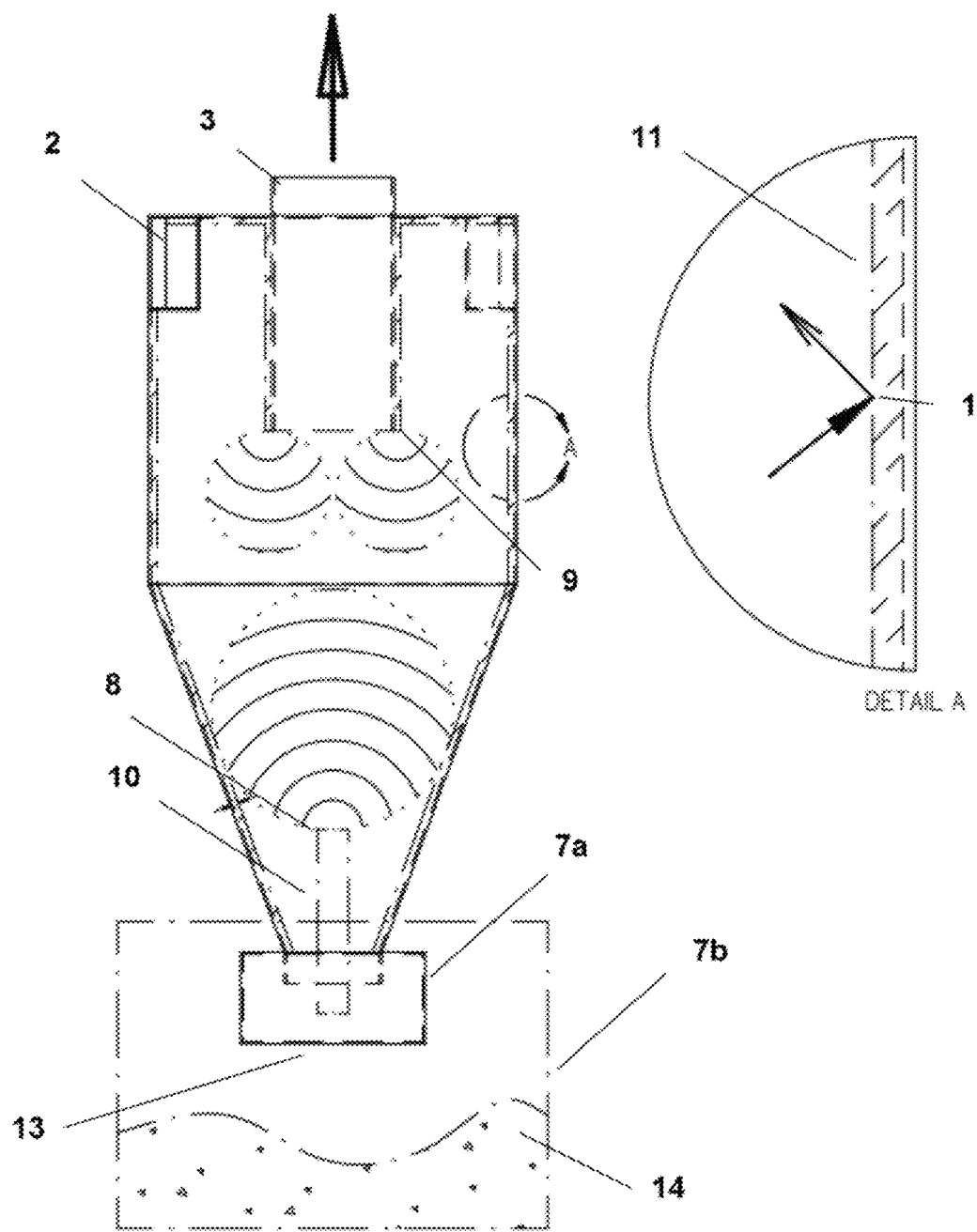
FIG. 2 shows a section view outlining the principal operation and fundamental construction of the ultraviolet cyclonic fluid dosing system according to one embodiment.
Figure 3:
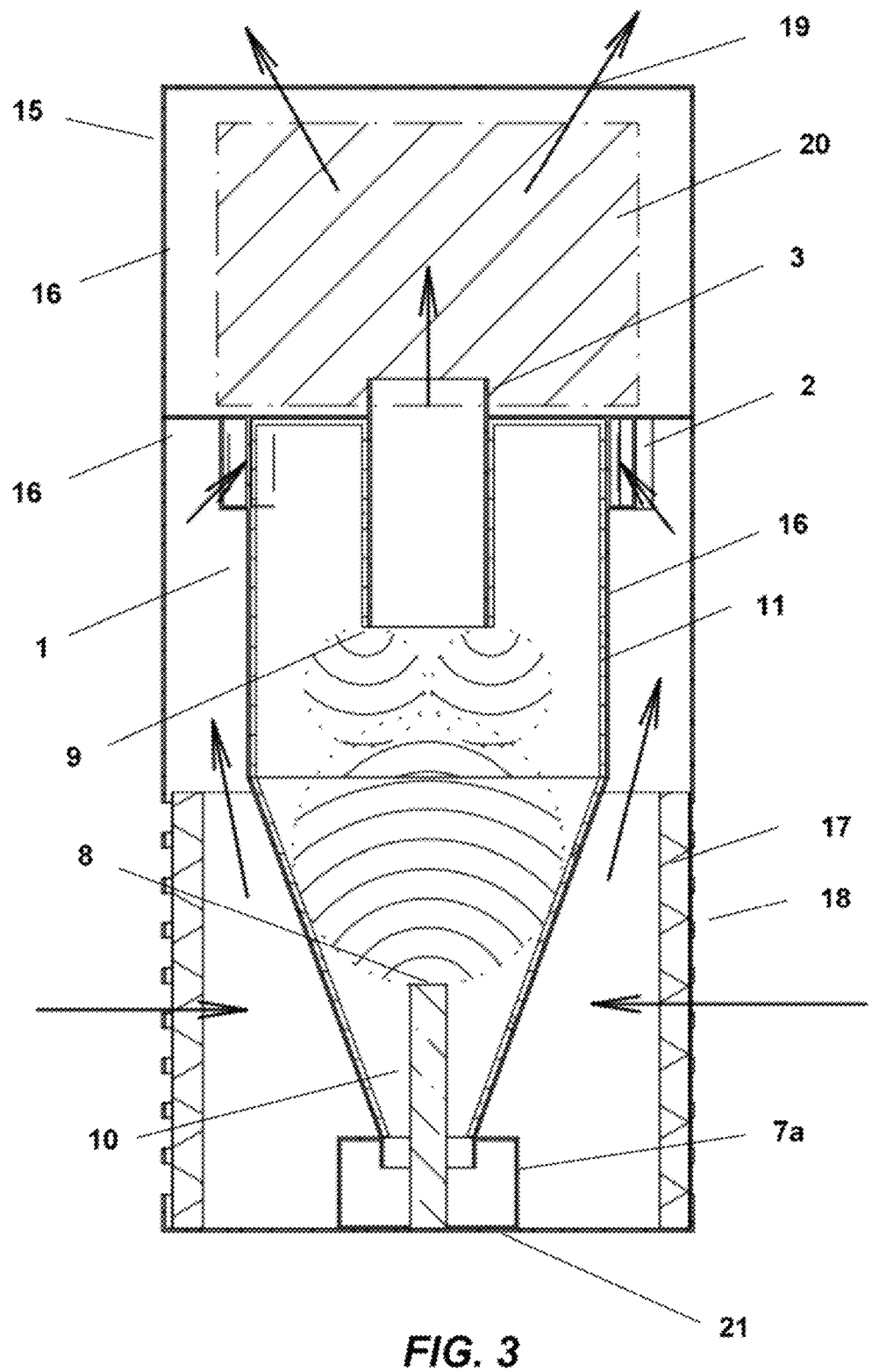
FIG. 3 illustrates the detailed construction and function of the ultraviolet cyclonic fluid dosing system applied in a single standalone domestic air disinfection configuration.
Figure 4:
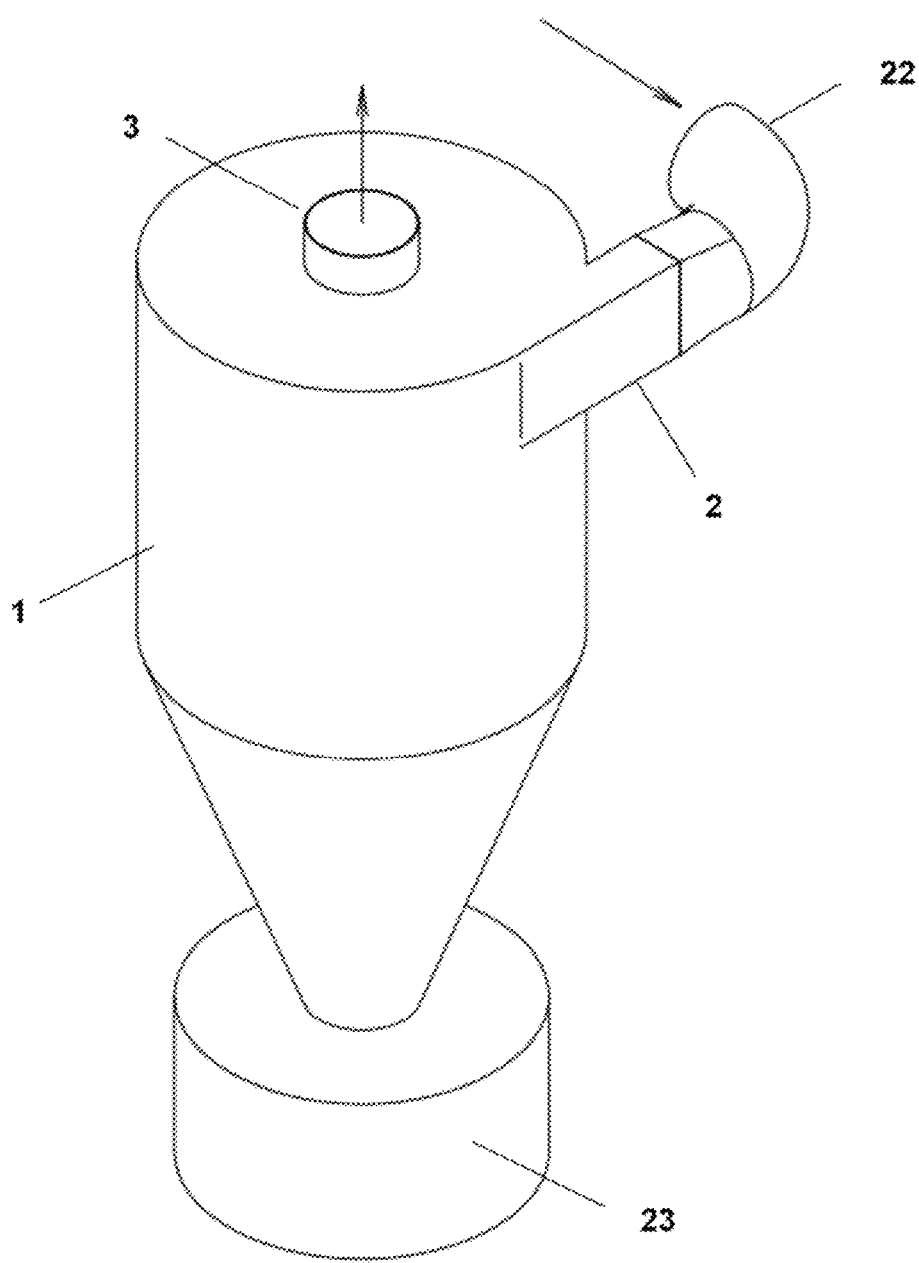
FIG. 4 illustrates the configuration difference when a single ultraviolet cyclonic fluid dosing system is used for liquid dosing or disinfection.
Figure 5:
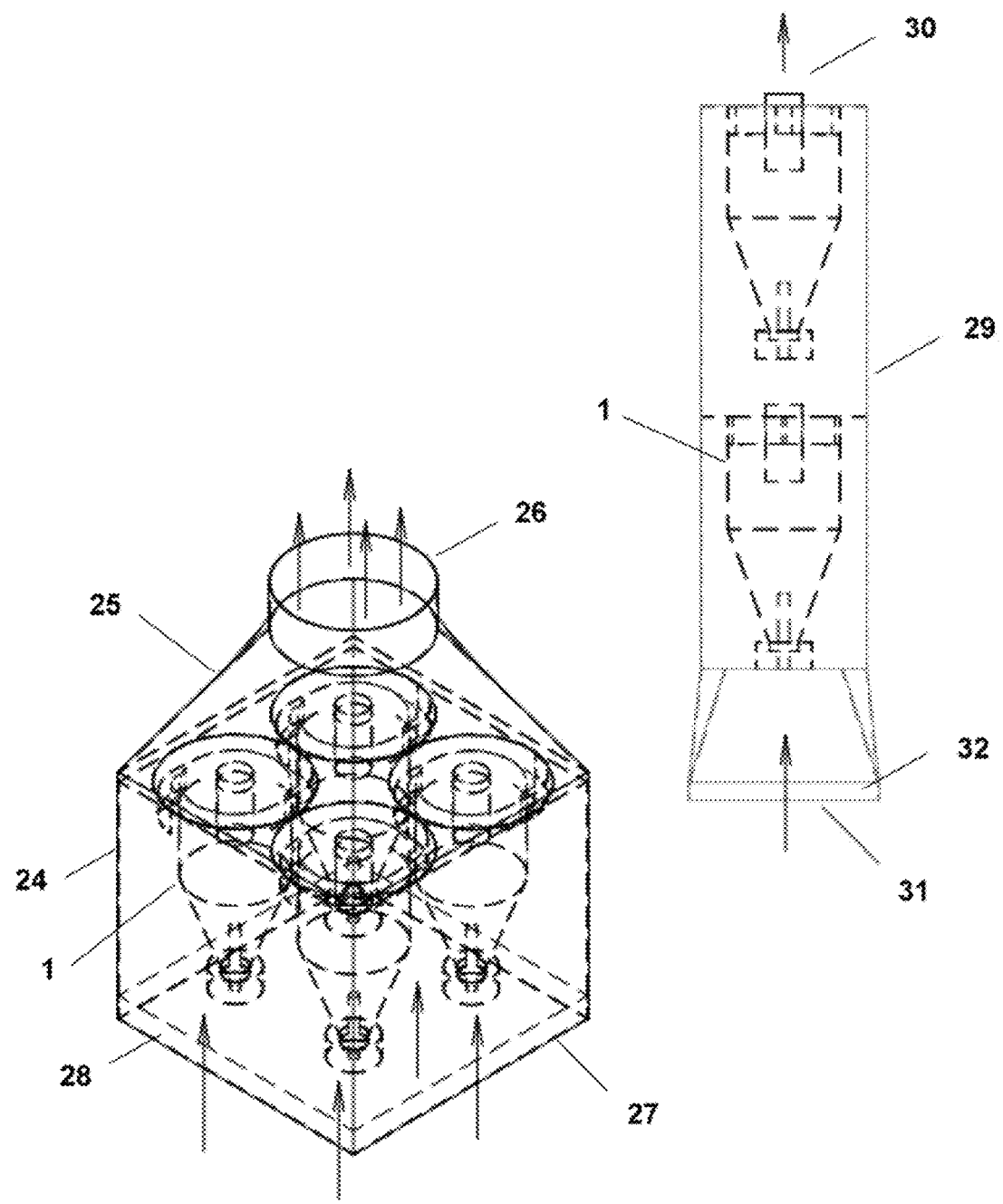
FIG. 5 shows ultraviolet cyclonic fluid dosing systems configured for air or gas dosing or disinfection, assembled in a series (upper right) and parallel (lower left) configuration.
Figure 6:
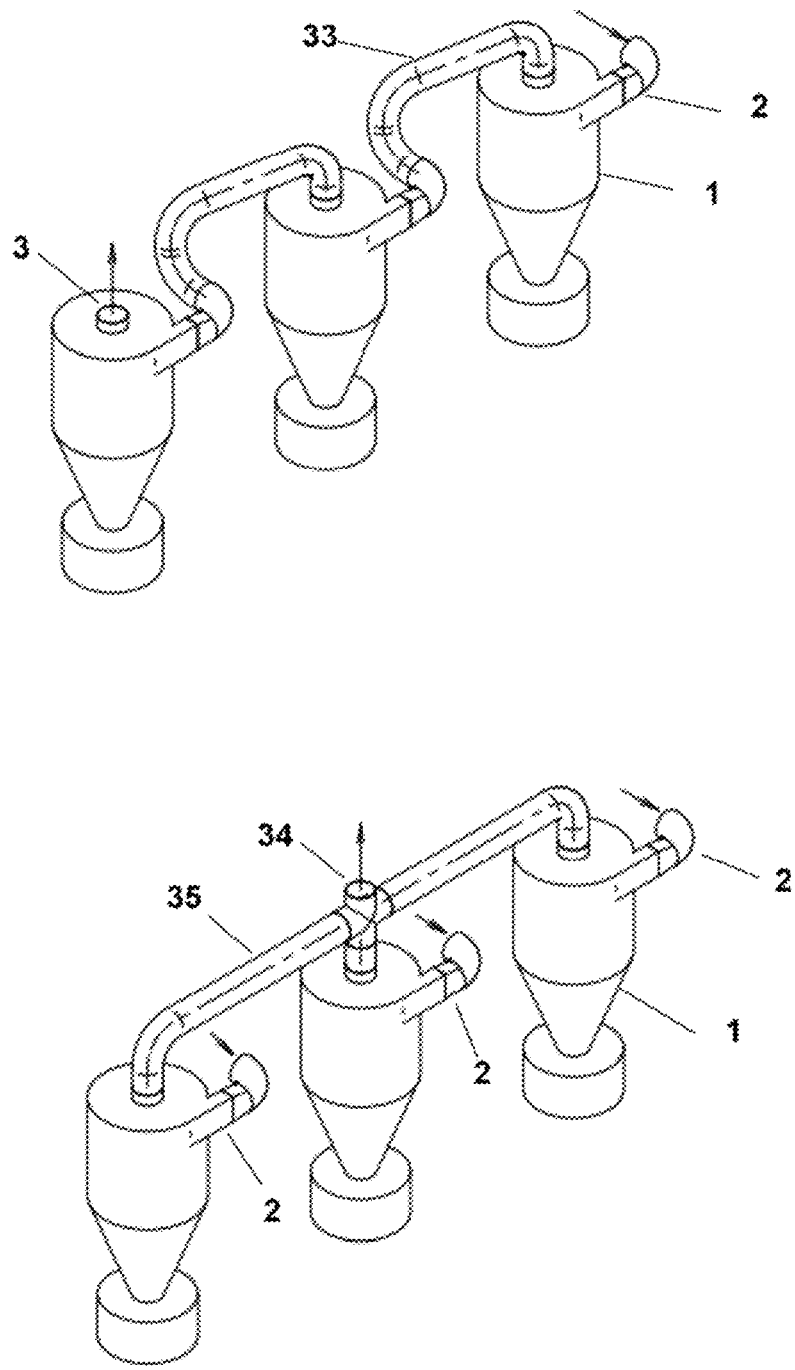
FIG. 6 shows ultraviolet cyclonic fluid dosing systems configured for water or liquid dosing or disinfection, assembled in a series (top) and parallel (bottom) configuration.
Figure 7:
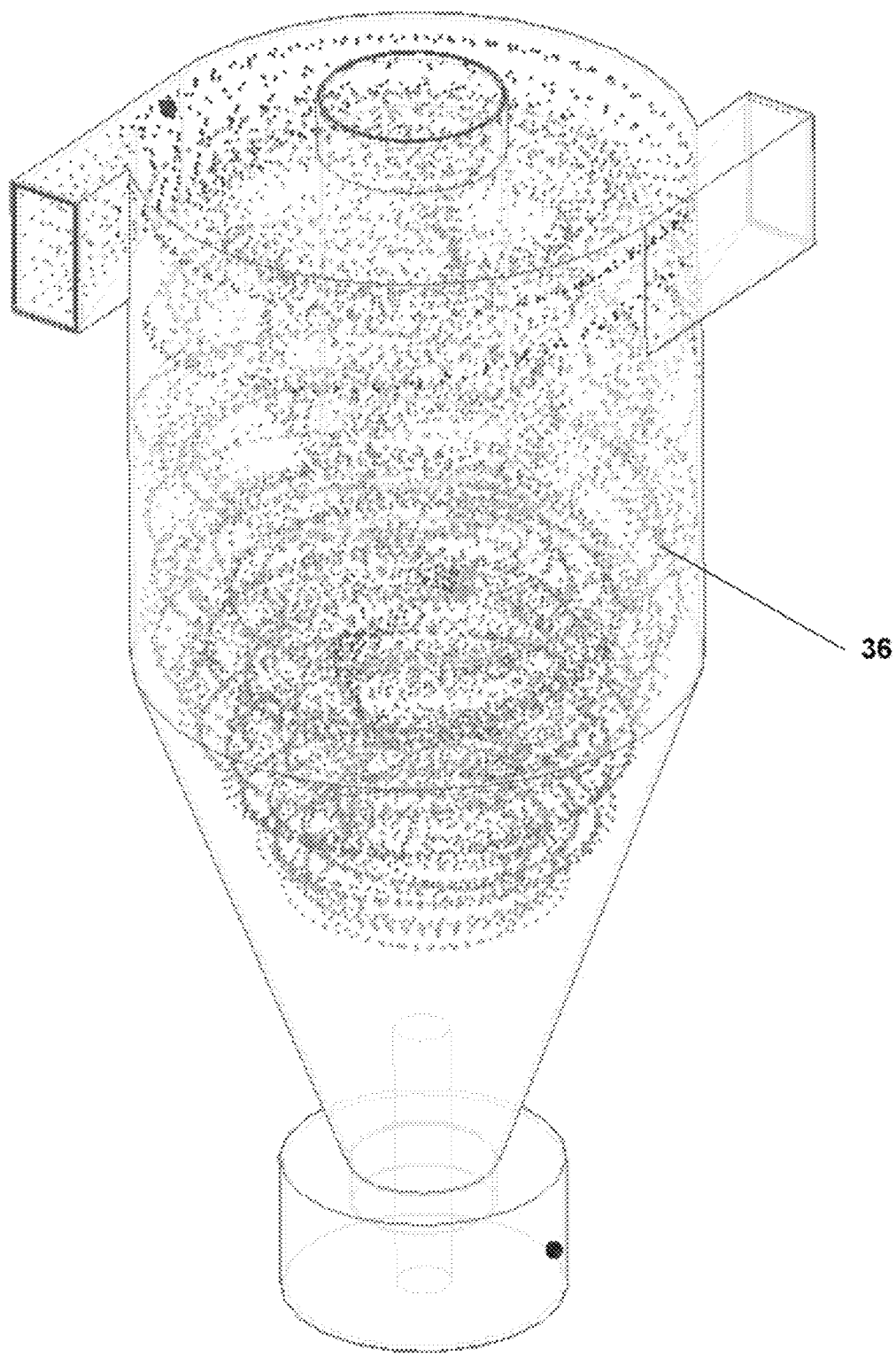
FIG. 7 illustrates the helical fluid flow path generated by the ultraviolet cyclonic fluid dosing system.
Figure 8:
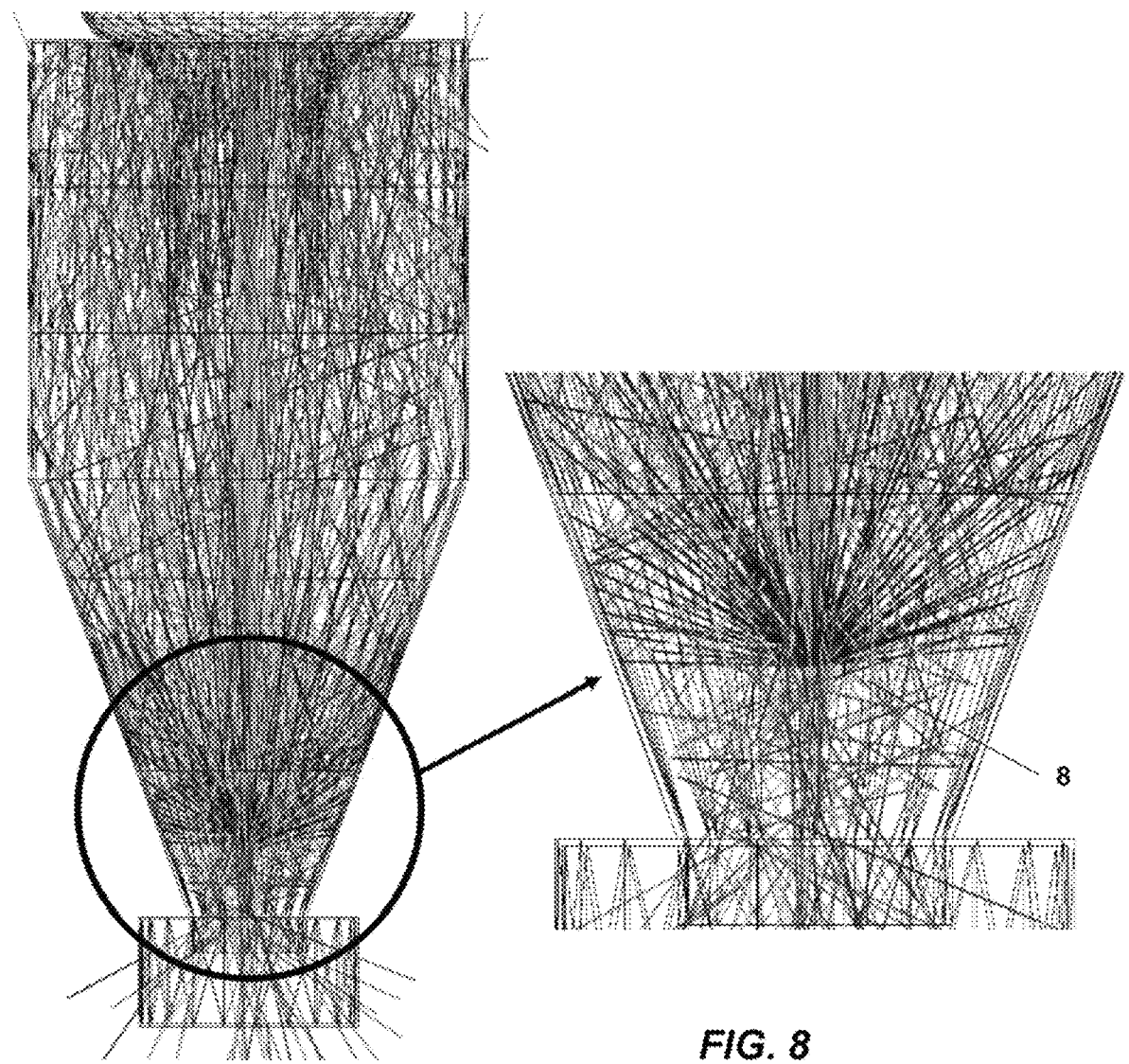
FIG. 8 illustrates the ultraviolet lights scattering behavior within the ultraviolet cyclonic dosing system due to the application of the ultraviolet reflective inner lining.
Figure 9B:
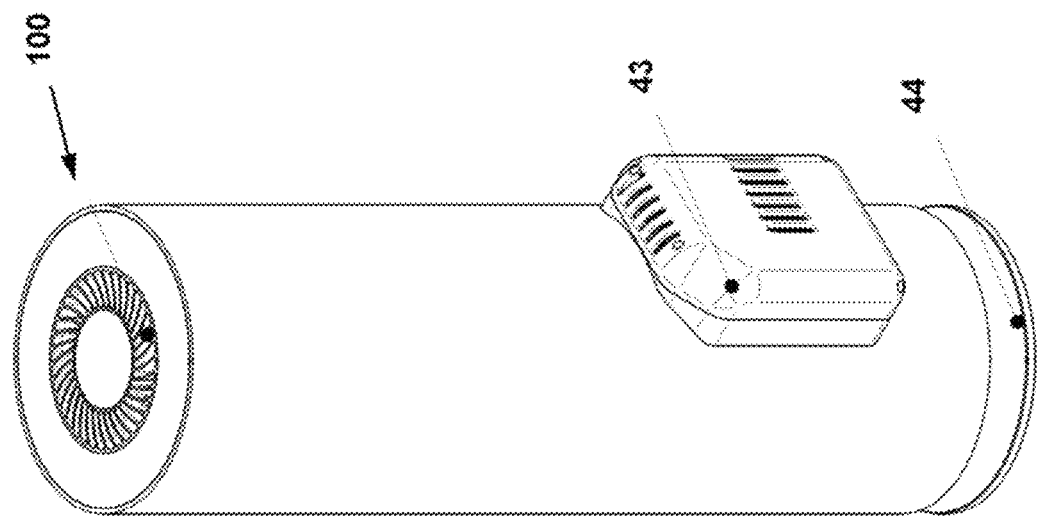
FIGS. 9A-9F illustrate views of an ultraviolet cyclonic fluid dosing system according to an example embodiment.
Figure 9A:
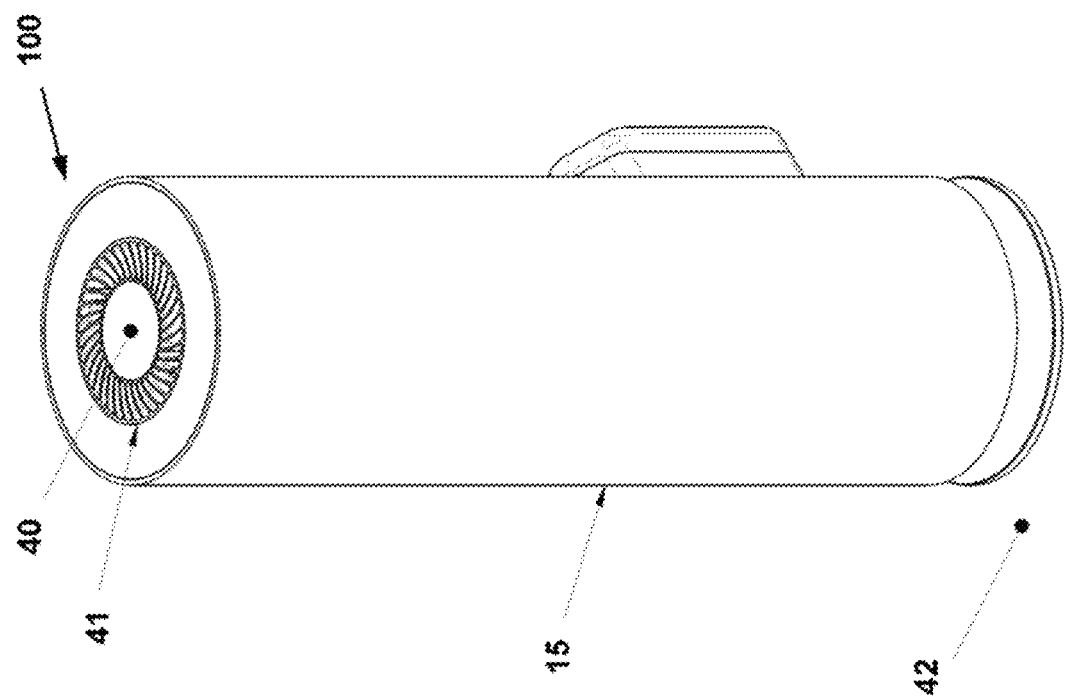

Embodiments of the invention provide a dose of ultraviolet light to a fluid that is pulled through the cyclonic dosing chamber. The typical use of this invention is to disinfect pathogens in fluids, such as water or air, although the invention can also be used to provide a dose of ultraviolet light to any fluid (liquid, gas, solids entrained in a fluid). An example embodiment is formed by the application of a cyclonic separator which has its internal volume illuminated with an ultraviolet light source. The intensity of the ultraviolet light within the cyclonic flow chamber is further increased by lining the inner surfaces of the cyclonic flow chamber with material highly reflective to ultraviolet light.

This invention addresses the disadvantages of prior art disinfection and dosing effectiveness of fluids by utilizing the long helical flow path created for a fluid within the relatively small cyclonic flow chamber. Due to the increased fluid flow path length, fluid residence time is proportionally increased. Utilization of this feature allows for greater than a single order of magnitude improvement of fluid residence time within the disinfection volume when compared to the prior art. With the addition of the ultraviolet reflective inner lining, the fluid will be treated with a higher dose of ultraviolet light relative to a prior art system of similar dosing volume and length, assuming an equal flow rate for both systems.

Embodiments of the invention operate by drawing fluid through the cyclonic flow chamber, which forces the fluid to travel in a helical flow path within the cyclonic chamber due to the chamber's internal geometry. The fluid flow path is tailored to maximize fluid residence time within the cyclonic chamber for the fluid the system is configured for. The residence time optimization is accomplished by adjusting the chamber's diameter, the length of the cylindrical chamber section, the length and angle of the lower conical chamber section, the number of inlets, the shape, area, and geometry of the inlet, and the diameter and length of the central outlet tube. The dosing of the fluid is performed in the internal volume of the chamber, which is illuminated by an ultraviolet light source and reflected by the ultraviolet reflective lining of the chamber's inner surfaces. Lining the internal volume of the chamber with an ultraviolet reflective material directly increases radiance within the chamber by allowing the emitted light to reflect within the chamber for a longer period of time before complete ultraviolet photo absorption. In embodiments that are configured for disinfection of pathogens in gases, most commonly air, the embodiments would be configured with an outer housing and support structure that contains the cyclonic chamber(s), ultraviolet light source(s), fan(s), the ultraviolet reflective lining within the cyclonic chamber(s), prefilter(s), and dust trap(s).

In typical embodiments, an outer housing and support structure is used to house either a single or multiple units as described herein. For the use case of gases, such as air, the housing and support structure is the exterior structure that supports all of the components necessary to perform ultraviolet dosing. In some instances, for a liquid use case, the housing is utilized to direct the fluid in through the device inlet, and out through the device outlet. The ultraviolet light source positioned inside of the cyclonic chamber can emit ultraviolet light from lamp(s), bulb(s), light emitting diode (s), laser elements or high intensity ultraviolet beams generated outside the cyclonic chamber and directed into the chamber. The ultraviolet light source(s) can be positioned protruding from the center of the dust or sediment traps, around the perimeters of the dust or sediment trap inlet, around the perimeters of the fluid outlet, protruding from the center of the of the fluid outlet, or at the cyclonic chamber wall emitting into the chamber. The ultraviolet reflective lining within the cyclonic chamber covers the internal surfaces to the maximum extent practical. The lining can be composed of highly UV reflective material such as sintered PTFE polymer, Barium Sulfate, or a compound containing both sintered PTFE and Barium Sulfate.

The prefilter is positioned near the inlet to allow removal of debris and particles before entering the cyclonic dosing chamber. The prefilter can be constructed from filter media, fiber material, membrane material, fabrics, foams, and/or meshes. The prefilter can be self-supporting or in a cartridge form contained in a secondary vessel.

The fan(s) or pump(s) are positioned downstream of the cyclonic dosing chamber to pull the fluid through the chamber. Fan(s) used can be axial, centrifugal or mixed flow type. They are selected to have relatively high flow rates and static pressure, which are the same selection criteria for pump(s) in liquid use-cases.

When configured for water or other liquid flow, device components would be identical, except for fluid pump(s) in lieu of fan(s) and sediment trap(s) in lieu of dust trap(s). Embodiments can be used as a single cyclonic chamber assembly, or can utilize multiple cyclonic chamber assemblies configured in series or in parallel tailored to meet the requirements of a specific use case. Series configuration would increase the dose to the fluid, and parallel configuration would increase the flow rate.

In all configurations (single, series, or parallel), use of the device is the same. Fan(s) or pump(s) are connected to the outlet. The fan(s) or pump(s) create a low local pressure within the cyclonic chamber and the fluid will flow through the cyclonic chamber in the helical flow path. The complete flow path starts at a prefilter near the device inlet. Debris and particulate are filtered from the fluid stream to protect cleanliness of the cyclonic dosing chamber and the ultraviolet light source. Exiting the prefilter, the fluid flow enters the device's external housing. The fluid flow is pulled into the cyclonic chamber through intake opening(s) that are designed to induce tangential flow within the chamber. This induction of tangential flow is what starts the helical flow path within the cyclonic chamber. The fluid and any pathogens begin to immediately receive a dose from the ultraviolet light emitted once entering the chamber. The dose received is increased by the recycled radiance from the ultraviolet reflective coating. The fluid and pathogens will continue to receive a dose of ultraviolet light while the fluid travels the helical flow path, finally reversing flow direction and exiting through the outlet to fan(s) or pump(s). Particulate or debris not collected by the prefilter will be collected in the dust trap(s) or sediment trap(s) present in the cyclonic separator, which protects the interior of the cyclonic chamber from erosion and maintains cleanliness of the ultraviolet light emitter(s) and the ultraviolet reflective lining. Embodiments can utilize an ultraviolet light intensity sensor to monitor the emitter's performance and relay system performance to the device user. The most basic application of this sensor is to verify the device is delivering the specified ultraviolet dose for the application. Additionally, the sensor could indicate to the user if the system requires maintenance or part replacement.

Embodiments of the invention, when used for domestic air disinfection, may contain sound absorbing and barrier material within the housing and on the exterior of the cyclonic dosing chamber to control sound emitted from the unit while in operation. Specially, sound control materials can be added around and within the fluid intake path, on the exterior of the cyclonic chamber, in and around the fluid outlet, and upstream and downstream of the fan.

While the main intended application for this invention is to disinfect air and water, the invention could also be implemented to disinfect any fluid. Another application outside of disinfection is dosing a fluid to achieve an altered physical state or characteristic. An example is using ultraviolet light to cure a fluid or solids entrained in fluid. Additionally, the invention could be used to perform chemical processing whereby a fluid is chemically altered from exposure to the ultraviolet light emitted.

FIG. 1 shows the principal components of the ultraviolet cyclonic fluid dosing system, and outlines the features of the cyclonic dosing chamber 1. The cyclonic dosing chamber 1 is composed of tangential fluid inlet(s) 2, a central fluid outlet 3, the upper cylindrical cyclonic chamber body 6, the lower conical cyclonic chamber body 5 and the lower dust or sediment trap 7. The cyclonic dosing chamber 1 creates the helical fluid flow path 36 illustrated in FIG. 7. The helical fluid flow path 36 is created through the configuration of each of the structures of FIGS. 1, 2, 3, 5 and 6. Each of the structures are configured to match specific desired fluid properties or flow rates. The tangential fluid inlet 2 induces the fluid into the cyclonic dosing chamber 1 in a tangential velocity vector. The tangential velocity vector is induced by the geometry of the fluid inlet 2. The central axis of flow of the inlet 2 is tangential to the circumference of the cylindrical body 6. Thus, as fluid in drawn into the chamber the vector of the fluid is at least initially tangent to the curve of the wall of the body 6. The initial tangential velocity component is fundamental to the performance of the dosing system. In some embodiments, inlet nozzles, or inlet guide vanes, further induce the tangential flow velocity component.

Once the fluid enters the cyclonic dosing chamber 1, the helical flow path 36 is created. The central fluid outlet 3 further helps induce the helical flow path 36. The central fluid outlet 3 penetration depth (shown in FIG. 2) into the cyclonic dosing chamber alters the flow path and is adjustable to create the optimal flow path for a given fluid. An optimal flow path is one where the fluid has the greatest residence time in the chamber while maintaining a stable flow. We have observed that a preferred flow path is induced by using a chamber with dimensions of 290-310 mm height (conical and cylindrical portions combined); 130-150 mm in diameter for the cylindrical portion; and a central outlet with the dimensions of 90-100 mm long with a 38-42 mm throat diameter. An example embodiment has a chamber that is 300 mm high/tall and 140 mm in diameter, a central outlet that is 92 mm long with a 40 mm throat diameter. In some embodiments, the preferred length of the central outlet may be in the range 60-70% of the length of the chamber. The upper cylindrical cyclonic chamber body 6 and the lower conical cyclonic chamber body 5 creates the helical flow path 36 by altering the fluid's tangential and radial velocity components. This behavior is fundamental to the operation of cyclonic separators. The ultraviolet cyclonic fluid dosing system utilizes the cyclonic separator behavior with the dust or sediment trap 7. The dust or sediment trap 7 allows particles and debris not captured in prefiltration to settle into the trap(s) once separated from the fluid stream. This feature ultimately preserves the effectiveness of the ultraviolet cyclonic fluid dosing system by preventing erosion from, and accumulation of, dust and debris collected by the system during operation. The most practical material for construction of the cyclonic dosing chamber would be, but is not limited to, metals, plastics, reinforced plastics, polymers, composite polymers, ceramics, glass, or a combination of these materials best suiting the application or the fluid.

FIG. 2 shows the principal operation of the ultraviolet cyclonic fluid dosing system through the detailed internal construction of the ultraviolet cyclonic fluid dosing system. Within the cyclonic dosing chamber 1 the system houses the ultraviolet light emitter(s) 8 and 9, the central light emitter pedestal 10, the penetrating central fluid outlet 3, and the ultraviolet reflective inner lining 11, which causes reflections 12 of the ultraviolet light emitted within the dosing chamber (Detail A). In a typical embodiment, the emitters are configured in a circular array, oriented downwards or upwards, and parallel with the central axis of the chamber. Additionally, shown in FIG. 2 is one configuration of the sediment and dust traps 7*a* and 7*b* respectively for gas and liquid operations. As shown in FIG. 2, fluid (liquid, gas, or entrained fluid) enters the cyclonic dosing chamber 1 through the tangential fluid inlet 2 and transitions into the helical fluid flow path 36 while gaining a dose of ultraviolet light emitted from the emitter(s) 8 and/or 9. The fluid flow path 36 traverses to the lower portion of the lower conical cyclone body section 5. The fluid stalls near the base of conical section 5 then transitions to vertical travel helically toward the central fluid outlet 3 and terminally exits the cyclonic dosing chamber. Once the fluid exits the central fluid outlet 3 the fluid will no longer receive a dose of ultraviolet light and the disinfecting or dosing process is considered complete. A downstream fan or pump will ultimately receive the fluid and discharge the fluid into the desired end environment.

The intensity of ultraviolet light within the cyclonic dosing chamber 1 is further increased by the ultraviolet reflective lining 11. The reflective inner lining 11 optimally covers the maximum extent of the inner surface of the cyclonic dosing chamber 1. Covering the maximum extent of the inner surface of the chamber 1 is not required, but preferred to minimize emitter cost/power output. Reduced reflector efficiency (due to extent or reflector material)

requires a corresponding increase in emitter output to achieve an effective dosage level. The ultraviolet reflective lining 11 is composed of highly UV reflective material such as sintered PTFE polymer, Barium Sulfate, or a combination of the two with or without binding agents. An expansive example of simulated behavior between the ultraviolet light emitted in the dosing chambers 1 and the inner ultraviolet reflective coating is seen in FIG. 8. The emitter is represented at the origin (convergence) of the blue lines. Scattered internal ultraviolet rays are illustrated by all of the varying-colored lines, with the exception of the black structural lines which are a representation of the cyclonic dosing chamber 1. Key features of this device include a combination of: illuminating the inner volume of the cyclonic dosing chamber 1 with ultraviolet light; the use of a cyclonic flow path generating chamber to increase the in-volume fluid residence time; and the increased intensity achieved from the ultraviolet reflective lining within the cyclonic dosing chamber 1. The ultraviolet emitters 8/9 are positioned and arranged within the cyclonic dosing chamber 1 to meet the dosing requirements of the fluid. The dosing requirement is process dependent so it will vary depending on the needs of the treatment and/or fluid. For an example air-cleaning application, we have identified a 300 mm chamber with a diameter of 140 mm with a 92 mm long central outlet with a diameter of 40 mm and 6-12 emitters. Other dimensions may be employed for other applications or embodiments. The ultraviolet light is illustrated in FIG. 2 by the arcing circles within the cyclonic dosing chamber 1. The ultraviolet light emitters are most commonly lamps, bulbs, or light emitting diodes, but in some embodiments, high intensity coupled ultraviolet lasers or beams are implemented to achieve a higher relative dose. FIG. 2 outlines the different configurations of dust and sediment traps 7*a* and 7*b*. The dust trap 7*a* is typically used for gas or air systems, and the larger sediment trap 7*b* is typically used for liquid systems. Sediment separated from the fluid stream in the cyclonic dosing chamber is accumulated in the sediment trap 14. Both configurations are designed with an accumulated material cleanout or service access 13.

FIG. 3 illustrates the implementation of the ultraviolet cyclonic fluid dosing system configured as a standalone domestic air disinfection system. The configuration in FIG. 3 shows a system housing 15, which contains and supports all of the system components, a prefilter 17, sound absorption and barrier material 16 throughout the systems internals, the complete complex of components from FIG. 2 to provide a disinfecting dose to the air pulled through the system, a fan or blower 20 that pulls disinfected air through the system and out of a directional outlet 19, and a service or dust removal hatch 21. A preferred embodiment employs acoustic foam and rubber as barrier material 16 to provide sound absorption and dampening, respectively.

Operation of the illustrated standalone domestic air disinfection system begins at the housing intake grate 18. When the fan or blower 20 is activated, the internal volume of the cyclonic dosing chamber, along with the lower section of the system housing 15, decreases in static pressure relative to the surroundings. Flow of un-disinfected air is pulled through the system filter 17 which removes entrained dust or particulate from the air. The purpose of the prefilter 17 is to mechanically filter the intake air to protect the internals of cyclonic dosing chamber 1, such as the inner reflective lining 11 and the ultraviolet light emitters 8/9. Consequently, the filter improves system longevity and dosing effectiveness by maintaining material cleanliness, which prevents blocking emittance or reflectance of UV light. As air enters the lower section of the housing, the internal surfaces are clad with sound damping material 16 to reduce general noise output of the device. The air is pulled up the housing 15 internals into the tangential fluid inlets 2 and processed within the cyclonic dosing chamber 1. The air is disinfected within the chamber, and pulled from the system by the fan or blower 20 out of the directional exhaust nozzle outlet 19. The system can be serviced, and the accumulated debris can be cleaned by accessing the service or cleanout hatch 21. This standalone air disinfector enables an effective dosing or inactivation of pathogens relative to prior art due to the unique use of the cyclonic dosing chamber 1 as outlined by the description of FIG. 2.

FIG. 4 illustrates the ultraviolet cyclonic fluid dosing system configured for ultraviolet dosing or disinfection of liquid. Configuration of the invention for dosing or disinfecting liquids is accomplished with a liquid-tight cyclonic dosing chamber 1, the addition of a larger sediment trap 23 and the fitment of liquid transfer fittings (pipe transitions fitting 22). The described configuration of FIG. 4, with the application of the cyclonic dosing chamber described in FIG. 2, is capable of dosing liquid by pulling fluid through the system. The pump shall be downstream of the system, and ultimately connected to the central outlet 3. The liquid enters at the system inlets 22, 2, then enters into the cyclonic dosing chamber 1, where the liquid receives the specified ultraviolet dose and exits through the outlet 3 into a downstream pump.

FIG. 5 illustrates the configuration of multiple ultraviolet cyclonic fluid dosing systems in series and parallel configurations for dosing or disinfecting of air or gases. The lower left illustration shows a parallel configuration where the unprocessed gas enters the parallel configuration housing 24 through the inlet filter 28 stowed by the service hatch 27. The gas enters the cyclonic dosing chambers 1 and exits into a duct transition adapter 25 and where the now disinfected or ultraviolet dosed air or gas exits into system ducting 26 and ultimately through a fan or blower. The duct transition adapter 25 is hermetically isolated from the parallel configuration housing 25, except with respect to flow through the central fluid outlets 3 into the adapter 25. The upper right illustration shows a series configuration where the unprocessed gas enters the series configuration housing 29 through the inlet filter 32 stowed by the service hatch 31. The gas enters the cyclonic dosing chambers 1 and exits through the device outlet 30. The upper and lower portions of the series configuration housing 29 are hermetically isolated from each other, except with respect to flow from the central fluid outlet 3 of the lower cyclonic housing being received in the upper portion of the housing 29. The now disinfected or ultraviolet dosed air or gas transitions into system ducting and ultimately through a fan or blower.

FIG. 6 is a similar illustration to the concepts illustrated by FIG. 5, with the exception of implementing a system designed for liquid processing. The lower illustration shows a parallel configuration, where the unprocessed liquid enters the inlets 2, enters the cyclonic dosing chambers 1, and exits into a parallel system manifold 35 that leads to the outlet 34, and ultimately, through a downstream pump. The upper illustration shows a series configuration, where the unprocessed liquid enters the first stage inlet 2, proceeds through the cyclonic dosing chambers 1, exits through the final stage outlet 3, and ultimately, through a downstream pump. With respect to the illustrations of FIGS. 5 and 6, series configurations achieve the advantage of higher relative dose to the fluid, and parallel configurations achieve the advantage of increased relative flow rate.

FIGS. 9A-9F illustrate views of an ultraviolet cyclonic fluid dosing system 100 according to an example embodiment. FIGS. 9A and 9B respectively illustrate front and rear isometric views of the dosing system 100. The illustrated system includes a housing 15, a user interface and display 40, a directional outlet 41, an air intake 42, an external power supply 43, and a pedestal 44.

Figure 9D:
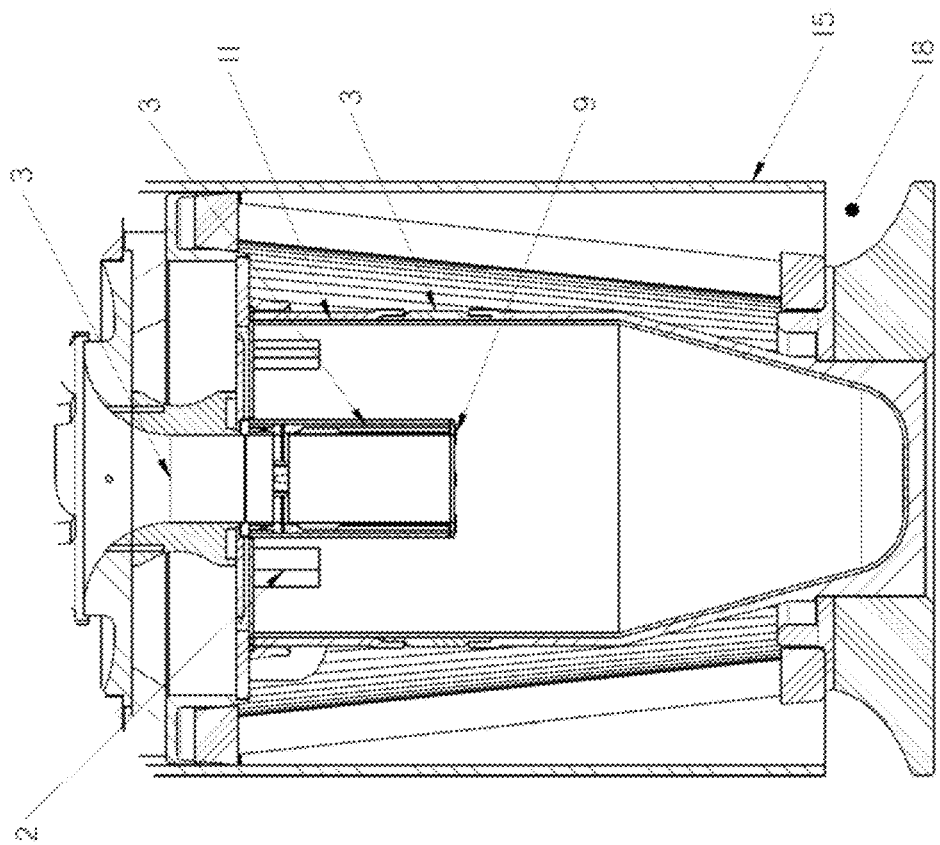
Figure 9C:
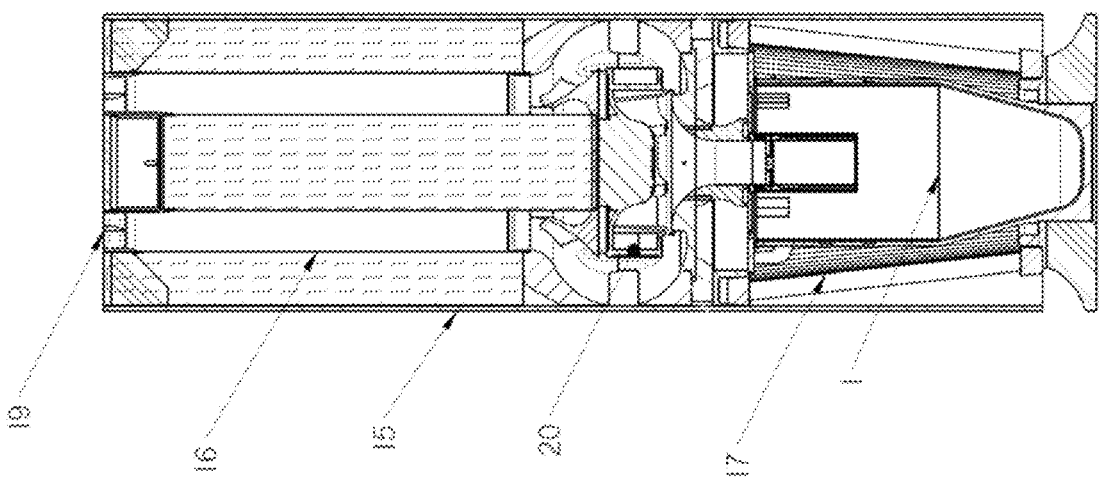

FIG. 9C shows a sectional view of the dosing system 100. This view shows the dosing chamber 1, system housing 15, sound absorption and barrier material (acoustic foam) 16, prefilter membrane 17, directional outlet 19, and blower 20.

FIG. 9D shows a sectional view of the lower portion of the dosing system, focusing on the dosing chamber 1 and its associated components. More particularly, this view shows the tangential intake nozzle 2, outlet 3, emitter array 9, reflective lining 11, lower portion of the housing 15, and intake 18.

Figure 9F:
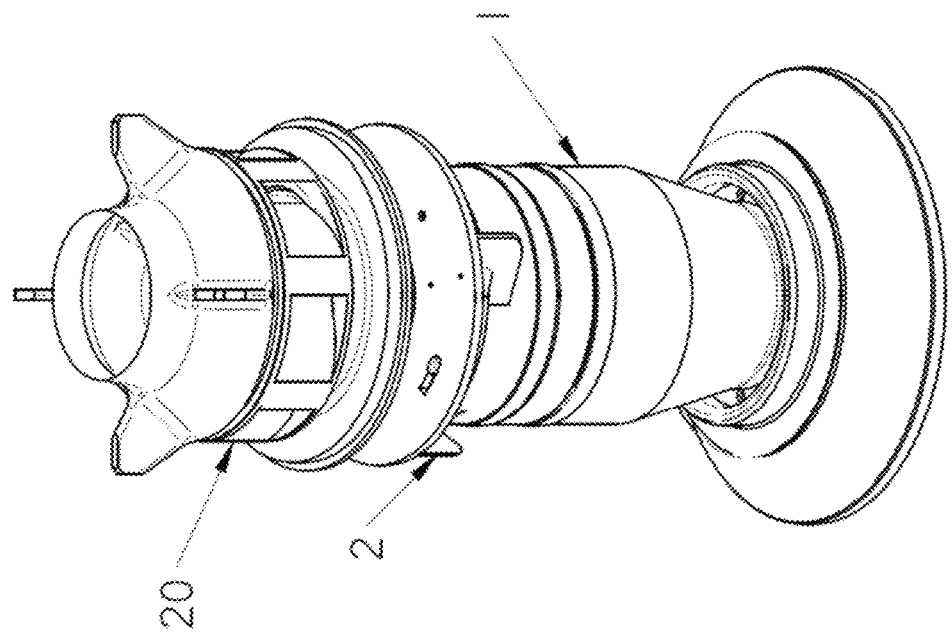
Figure 9E:
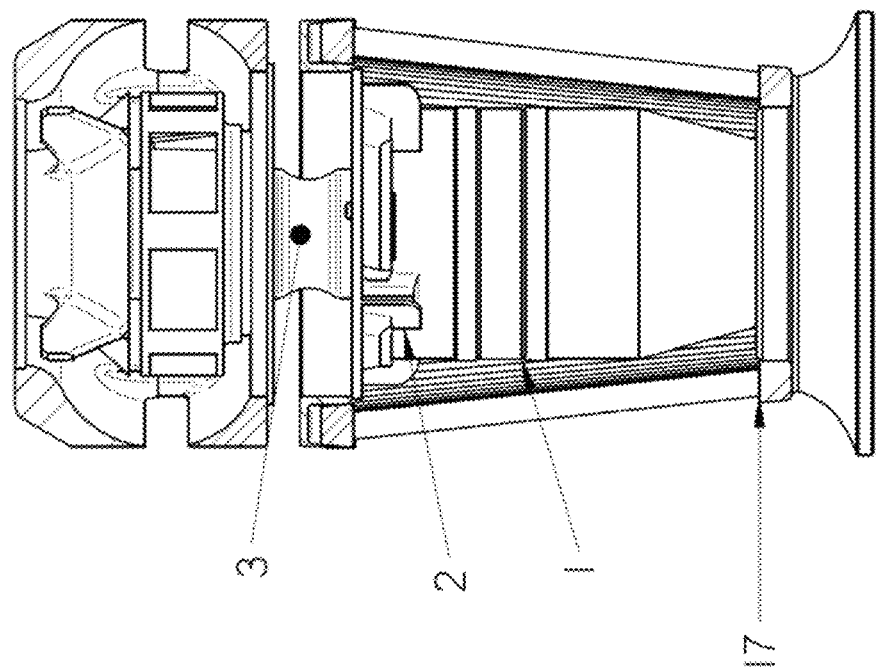

FIG. 9E shows a sectional view of the blower assembly above the dosing chamber 1. The chamber 1, tangential intake nozzles 2, outlet 3, and prefilter 17 are visible in this view.

FIG. 9F shows an isometric view of the blower assembly and dosing chamber with the housing removed. The chamber 1, tangential intake nozzles 2, and blower 20 are visible in this view.

As used herein, ultraviolet (UV) light is understood generally to be electromagnetic radiation having a wavelength in the range 10-400 nm. Typical embodiments will employ UV-C radiation, in the range of 200-280 nm, although the invention is not limited to UV radiation in that specific range. In some embodiments, multiple different wavelengths of UV light may be employed, for example by using a broad-spectrum light source or by using multiple light sources each having different specific peak wavelengths. In addition, some embodiments instead or in addition employ radiation having wavelengths outside of the UV range, such as gamma rays.

All of the above U.S. patents, U.S. patent application publications, U.S. patent applications, foreign patents, foreign patent applications and non-patent publications referred to in this specification and/or listed in the Application Data Sheet, including but not limited to U.S. Provisional Patent Application No. 63/136,637, entitled "ULTRAVIOLET CYCLONIC FLUID DOSING SYSTEM," filed Jan. 12, 2021, are incorporated herein by reference, in their entireties.

From the foregoing it will be appreciated that although specific embodiments have been described herein for purposes of illustration, various modifications may be made without deviating from the spirit and scope of the invention. Accordingly, the scope of the invention is determined by the claims and not limited by the disclosure of the specific embodiments above.

The invention claimed is:

1. An ultraviolet cyclonic fluid dosing system, comprising:

a dosing chamber comprising:

an upper cylindrical cyclonic chamber defining a central axis and having a tangential fluid inlet and a cylindrical fluid outlet, wherein the cylindrical fluid outlet has a central axis that is aligned with the central axis of the cylindrical cyclonic chamber, wherein the cylindrical fluid outlet extends downward from along the central axis to define a fluid outlet that is lower than the fluid inlet;

a lower conical cyclonic chamber coupled to the upper chamber and having a central axis that is aligned with the central axis of the upper cylindrical chamber;

an array of ultraviolet-light emitters disposed in the upper chamber along a circumferential perimeter of the cylindrical fluid outlet, wherein the ultraviolet-light emitters of the array point towards the lower chamber; and an ultraviolet-light emitter disposed in the lower chamber along the central axis, wherein the ultraviolet-light emitter points towards the upper chamber, wherein the emitters are configured to dose a fluid material with ultraviolet light, wherein the fluid material enters the fluid inlet and travels through a helical path through the dosing chamber.

2. The system of claim 1, wherein the upper and lower chambers are coated on an inner surface with a reflective material.

3. The system of claim 2, wherein the reflective material includes one or more of sintered PTFE polymer and Barium Sulfate.

4. The system of claim 1, wherein the fluid material is air.

5. The system of claim 1, wherein the fluid material is water.

6. The system of claim 1, wherein the chamber is configured to cause the fluid material to travel in a helical path downwards through the upper chamber and then downwards into the lower chamber, where the fluid material transitions to travel upwards and exit the central fluid outlet.

7. The system of claim 3, further comprising one or more additional dosing chambers, each including at least one ultraviolet light emitter.

8. The system of claim 7, wherein the dosing chambers are connected in parallel, such that a quantity of fluid input to the system is divided amongst the dosing chambers.

9. The system of claim 7, wherein the dosing chambers are connected in series, such that a quantity of fluid input into the system passes through each of the dosing chambers in sequence.

10. An electromagnetic cyclonic fluid dosing system, comprising:

a dosing chamber comprising:

an upper cylindrical cyclonic chamber having a first end, a second end, a tangential fluid inlet, and a cylindrical central fluid outlet, wherein the central fluid outlet is positioned at the first end of the cylindrical chamber;

a lower conical cyclonic chamber having a first end and a narrower second end, wherein the first end of the lower chamber is coupled to the second end of the upper chamber;

an array of electromagnetic radiation emitters positioned within the dosing chamber along a circumferential perimeter of the cylindrical central fluid outlet and pointing towards the lower chamber; and an electromagnetic radiation emitter positioned in the lower chamber and pointing towards the upper chamber, the emitters configured to dose a fluid material with electromagnetic radiation, wherein the chamber is configured to cause the fluid material to travel in a helical path downwards from the first end of the upper chamber, through the upper chamber and then downwards through the second end of the upper chamber and into the lower chamber, where the fluid material transitions to travel upwards and exit the central fluid outlet.

11. The dosing system of claim 10, wherein the electromagnetic radiation is one or more of ultraviolet light or gamma radiation.

12. The dosing system of claim 10, wherein the upper chamber has a diameter of 130-150 mm.

13. The dosing system of claim 10, wherein the upper and lower chambers together have a length of 290-310 mm.

14. The dosing system of claim 10, wherein the cylindrical central fluid outlet has a length of 90-100 mm and a diameter of 38-42 mm.

15. A cyclonic system for disinfecting air, the system comprising:

a dosing chamber having an upper portion and a lower portion coupled to the upper portion, the upper portion having a cylindrical inner surface, the lower portion having a conical inner surface, the upper portion defining an air inlet and an air outlet, the dosing chamber defining a central axis that extends through an upper interior space defined by the center of the upper portion and a lower interior space defined by the center of the lower portion and that intersects the air outlet, the air inlet disposed closer to the cylindrical inner surface than the central axis and configured to introduce air into the upper portion such that the air travels about the central axis along the cylindrical inner surface of the upper portion at a downward angle to the lower portion and, after the air reaches the lower portion, travels along the central axis through the upper portion to the air outlet to exit the dosing chamber, whereby a duration that the air spends in the lower portion and about the air outlet is increased, wherein the upper portion includes a cylindrical air outlet having a central axis aligned with the central axis of the dosing chamber, wherein the cylindrical air outlet extends downward from a top of the upper portion to define the air outlet lower than the air inlet;

an array of ultraviolet-light emitters disposed in the upper portion along a circumferential perimeter of the cylindrical air outlet, wherein the ultraviolet-light emitters of the array point towards the lower portion; and an ultraviolet-light emitter disposed in the lower portion along the central axis, wherein the ultraviolet-light emitter points towards the upper portion.

16. The system of claim 15, wherein the lower portion includes an extension that protrudes along the central axis from a bottom of the lower portion and that supports the ultraviolet-light emitter disposed in the lower portion, whereby cyclonic flow of the air is increased and an exposure time of the air to ultraviolet light is increased.

17. The system of claim 16, wherein the cylindrical inner surface and the conical inner surface are defined by a reflective material, whereby an amplitude of ultraviolet light in the upper chamber and the lower chamber is increased.

18. The system of claim 17, further comprising a housing that surrounds the dosing chamber, the housing defining a bottom opening and inner space disposed between the housing and the dosing chamber, the bottom opening containing a filter configured to mechanically filter air entering the housing, the inner space fluidly coupling the filter and the air inlet.

19. The system of claim 18, further comprising a sound damping material that lines a surface of the housing.

* * * * *

UNITED STATES PATENT AND TRADEMARK OFFICE
CERTIFICATE OF CORRECTION

PATENT NO. : 12,133,938 B2
APPLICATION NO. : 17/574159
DATED : November 5, 2024
INVENTOR(S) : Branden Lee Doyle et al.

It is certified that error appears in the above-identified patent and that said Letters Patent is hereby corrected as shown below:

In the Claims

In Column 12, Line 31 (Claim 7), "3" should read --1--.

Signed and Sealed this
Fourth Day of February, 2025

Coke Morgan Stewart
*Acting Director of the United States Patent and Trademark Office*